United States Patent
Petras et al.

(10) Patent No.: US 11,434,096 B2
(45) Date of Patent: Sep. 6, 2022

(54) ADAPTIVE SHEET CALIPER CONTROL SYSTEM AND APPARATUS AND METHODS

(71) Applicant: Kimberly-Clark Worldwide, Inc., Neenah, WI (US)

(72) Inventors: Ryan A. Petras, Sherwood, WI (US); Matthew W. Trautschold, Appleton, WI (US); Mark G. Dollevoet, Appleton, WI (US); Vivek M. Karandikar, Neenah, WI (US); Julie A. Hansen, Appleton, WI (US); Walter F. Montgomery, Broken Arrow, OK (US); Antwain Taylor, Martinez, GA (US); Kevin B. Sartain, Evans, GA (US); Justin P. Stergar, Aiken, SC (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 196 days.

(21) Appl. No.: 16/897,790

(22) Filed: Jun. 10, 2020

(65) Prior Publication Data
US 2020/0385227 A1  Dec. 10, 2020

Related U.S. Application Data

(60) Provisional application No. 62/859,325, filed on Jun. 10, 2019.

(51) Int. Cl.
*B65H 18/26* (2006.01)

(52) U.S. Cl.
CPC ....... *B65H 18/26* (2013.01); *B65H 2301/414* (2013.01); *B65H 2515/314* (2013.01); *B65H 2515/84* (2013.01)

(58) Field of Classification Search
CPC ........ B65H 18/26; B65H 20/02; B65H 19/30; B65H 2301/414; B65H 2515/84; B65H 2515/314
See application file for complete search history.

(56) References Cited

U.S. PATENT DOCUMENTS

| | | | |
|---|---|---|---|
| 7,104,031 B2 * | 9/2006 | Baggot | B65B 63/02 53/550 |
| 7,127,951 B2 * | 10/2006 | Sartain | B65H 26/00 73/818 |
| 7,204,154 B2 | 4/2007 | Sartain et al. | |
| 2017/0327337 A1 | 11/2017 | Bixler et al. | |

* cited by examiner

*Primary Examiner* — Sang K Kim
(74) *Attorney, Agent, or Firm* — Kimberly-Clark Worldwide, Inc.

(57) ABSTRACT

The present invention provides an adaptive control system to control a plant using direct output feedback in which a function of the full plant state, as opposed to estimates thereof, is used for feedback control of the plant. The adaptive control system of this invention is therefore highly useful in the control of plants, particularly plants for controlling the physical properties of rolls of web material and more particularly a calendering apparatus. Accordingly, in a particularly preferred embodiment the adaptive control system of this invention controls loading of a calender apparatus, such as a pair of opposed rolls forming a calendering stack, based upon the physical properties of a previously processed web.

19 Claims, 10 Drawing Sheets

ADAPTIVE SHEET CALIPER CONTROL SYSTEM AND APPARATUS AND METHODS

RELATED APPLICATIONS

The present application claims priority to U.S. Provisional Application No. 62/859,326, filed on Jun. 10, 2019, the contents of which are hereby incorporated by reference in a manner consistent with the present application.

BACKGROUND

In the manufacture of paper products, such as tissue products, paper webs are typically formed into large supply rolls, also referred to as parent rolls, after being manufactured and then subjected to further converting to produce a finished product. For example, a parent roll may unwound, calendered and rewound about a core to produce smaller sized rolls, which are generally more useful for use by a consumer. For example, in conventional systems, a core is often placed onto a mandrel that is capable of spinning so that the spinning of the mandrel in conjunction with the core can effectuate winding of the paper web thereon.

In certain instances, however, when parent rolls are formed into individual finished rolled products, the inner layers of the rolled product may tend to lose a noticeable amount of bulk due to the compressive forces that are exerted on the base web. Lowering bulk can reduce the perceived quality of the product. As such, a need currently exists for a process and system that controls the winding process to control bulk reduction.

Another problem experienced in the formation of wound products is in producing multiple rolls of material that all have a diameter and roll firmness within desired limits. Ideally, the rolled products should have a substantially uniform diameter and roll firmness so that there is no consumer noticed differences between the rolls. Further, consumers desire rolled products, especially rolled tissue products, to have a roll firmness within a desired range such that the rolls do not feel too hard or too "mushy".

The ability to form rolled products having a substantially uniform diameter and roll firmness also provide various other benefits during production of the product. For instance, controlling roll firmness can, in some applications, increase throughput efficiency. Further, uniform products can be easier to package, eliminating or reducing packaging delays that may occur if the rolls were formed with irregular properties.

In the past, one method of measuring roll firmness was to use a measuring system as described, for instance, in U.S. Pat. No. 7,204,154 to Sartain et al., which is hereby incorporated by reference in a manner consistent with the present disclosure. The roll firmness measuring system disclosed in the Sartain patent is designed to measure the roll firmness of selected rolls in an on-line fashion. Unfortunately, once measurements are taken, it is sometimes difficult to use the data for modifying process conditions to improve the quality of products produced.

As such, a need currently exists for a system for measuring and controlling important finished rolled product properties such as roll firmness and caliper.

SUMMARY

The present invention provides adaptive sheet caliper control systems, apparatus controlled by such systems and methods of modifying the caliper of a sheet using the same.

The present control systems, apparatus and methods are improvements upon prior art systems as they provide an adaptive control system to control a plant using direct output feedback. The direct output feedback is used in real time to control the system to a desired operating state. The adaptive control system of this invention is therefore highly useful in the control of plants, particularly plants for controlling the sheet caliper such as, for example, a calendering apparatus, a laminating apparatus or an embossing apparatus.

Thus, in one embodiment, the present invention provides a system for controlling a calendering apparatus, the system comprising an adaptive controller comprising an adaptive component and a gain-scheduled calender load controller, a caliper sensor and an actuator. In other embodiments the system may further comprise a load sensor, and more particularly a load sensor configured to detect the log spring constant of a finished rolled product, and a log spring constant cascade controller. In still other embodiments the system may further comprise a sensor for measuring the diameter of a parent roll being unwound to form a plurality of spirally wound finished rolled tissue products. In this manner, the apparatus may further comprise a winder and a winding cam for winding a plurality of rolled tissue products from the parent roll.

In another embodiment, the present invention provides a method for operating a system which regulates the load applied to a calender apparatus during the converting of a parent roll of spirally wound sheet material and having a parent roll diameter into individual finished rolled products of spirally wound sheet material comprising the steps: providing a first operating state of the system to regulate the load applied by the calender apparatus depending upon the diameter of the parent roll; sensing at least one characteristic of the finished rolled product with a sensor and generating at least one sensor output; communicating the at least one sensor output; receiving the at least one sensor output; using the at least one sensor output in an adaptive control scheme to determine the load to be applied by the calender apparatus in a second operating state of the system; and adjusting the load applied by the calender apparatus according to the second operating state.

In yet another embodiment, the present invention provides a system for regulating the load applied to a calender apparatus during the converting of a parent roll into individual finished rolled products, the system comprising: one or more sensor interfaces for receiving sensor outputs from a plurality of sensors that sense characteristics of the individual finished rolled products; a processing circuit configured to provide a first operating state wherein the calender apparatus is operated to vary the load applied by the calender apparatus to the unwound web dependent upon the diameter of the parent roll being unwound; wherein the processing circuit is configured to receive the sensor inputs from the one or more sensor interfaces and to determine and adjust the first operating state using an adaptive control scheme to an at least one adapted operating state; wherein the processing circuit is further configured to cause the system to transition from the first operating state to the at least one adapted operating state.

In still other embodiments the present invention provides a system for regulating the load applied to a calender apparatus during the converting of a parent roll into individual finished rolled products, the system comprising: an adaptive controller comprising a reference model, a parameter adjustment mechanism and a calender load control; an actuator for controlling the position of at least one calender roll in a calender stack; a caliper sensor for sensing the caliper of a calendered web; a load sensor for sensing a force applied to a contact element by a finished rolled product when the finished rolled product is placed in between the contact element and a support surface; a log spring constant cascade controller; wherein the adaptive controller is in communication with the actuator and configured to control the actuator for increasing or decreasing the caliper of a web of material based upon inputs from the caliper sensor and the load sensor.

DEFINITIONS

Figure 1:
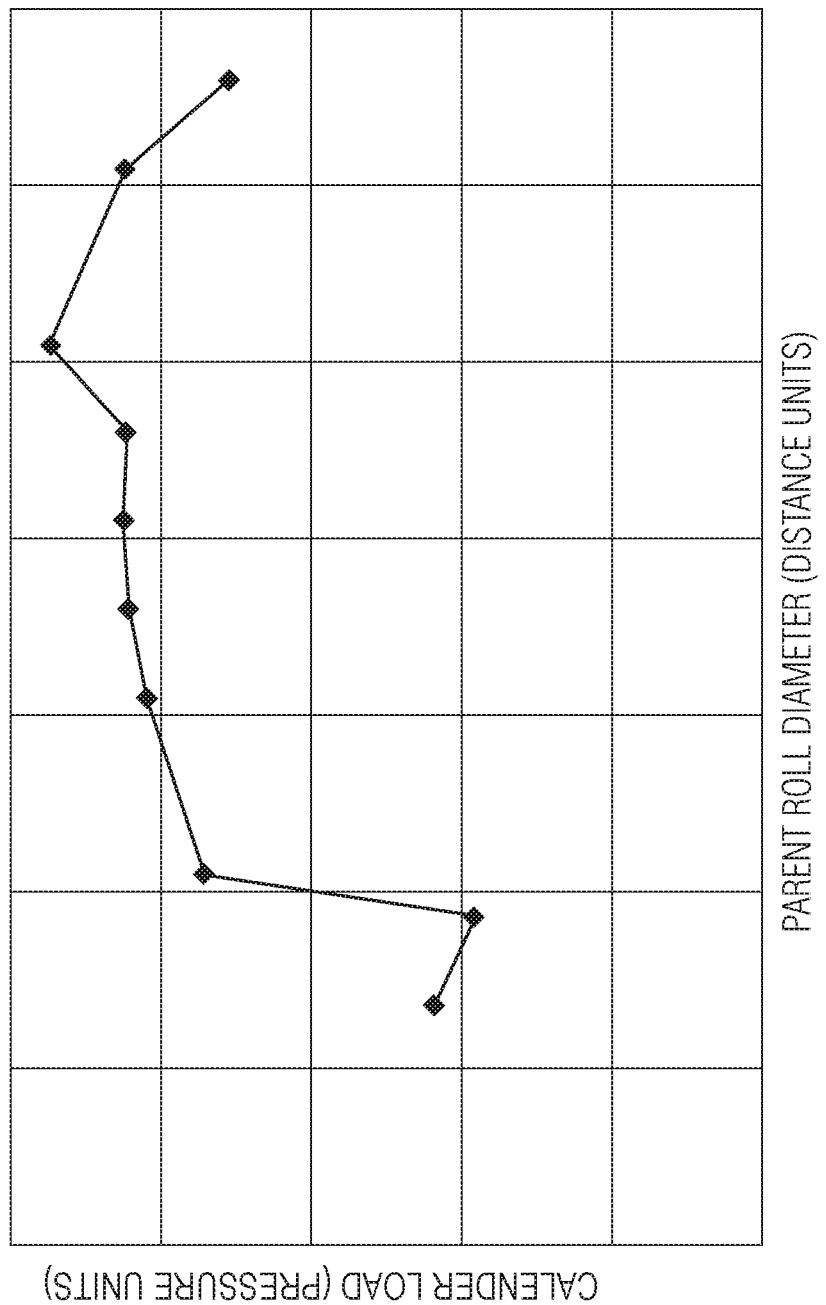
FIG. 1 a graph of calender load versus parent roll diameter.

As used herein the term "actuator" generally refers to any device capable of affecting the state of a plant to control one or more degrees of freedom thereof. Such actuator can be a motor, motor-driven screw, a hydraulic cylinder, a pump or valve controlling a stream of air, a compressor or suction generator, or other device.

As used herein the term "caliper" generally refers to z-directional thickness of a sheet material, such as a tissue product. Caliper may be measured using full contact, semi-contact, or contactless sensors as known in the art. Caliper generally has units of millimeters (mm) or microns (μm).

As used herein the term "compression ratio" generally refers to the ratio of sheet caliper compared to a theoretical caliper of the sheet required to achieve zero compression under a load. The compression ratio may be used to calculate the sheet caliper needed to achieve a desired log spring constant when a given sheet is spirally wound into a rolled product. Generally, a sheet having a greater caliper will have a greater compression ratio resulting in a greater log spring constant when the sheet is spirally wound into a rolled product. Compression ratio may be calculated based upon measured sheet caliper ($C_{SP}$) and the theoretical caliper of the same sheet ($C_T$) as shown in Equation 1, below.

$$\text{Compression Ratio} = 100 \times \left( \frac{C_{SP}}{C_T} - 1 \right) \qquad \text{Equation 1}$$

As used herein the term "direct output feedback" refers to a control system, apparatus or method that employs feedback of an output that is a function of the full state(s) existing in a plant. "Direct" refers to the fact that no state estimation is used to estimate plant states not present in or not derivable from the "output."

As used herein the term "firmness" generally refers to the compressibility of a rolled product in a direction normal to its longitudinal axis. Generally, a rolled product having a high degree of firmness will be less compressible.

As used herein the term "log spring constant" refers to the force required to impinge a device a given distance into a rolled product and generally has units of force per unit distance, such as Newtons per millimeter (N/mm). Generally, a rolled product having a high degree of firmness will be less compressible and have a greater log spring constant than a rolled product that is compressible and has a low degree of firmness.

An "operator" generally interacts with the system and provides an input thereto and may be a human or computer. The operator may interface with the system via an operative link configured to communicate with one or more control commands. The operative link may comprise a serial connection (wired and/or wireless), according to some implementations. The one or more control commands may be stored in a command file (e.g., a script file). The file may be communicated to the system using any of the applicable interfaces (e.g., a serial link, a microcontroller, flash memory card inserted into the robot, and/or other interfaces).

As used herein the term "plant" generally refers to a system controlled by a control system. For example, the plant can be a system for converting a parent roll of sheet material to individual rolled products. In certain preferred embodiments the plant may comprise one or more converting unit operations including, without limitation, calendering, slitting, perforating, folding, embossing, laminating, printing, plying and winding. One or more of these unit operations may be useful in converting a sheet material from a parent roll to a finished rolled product.

As used herein the term "rolled product" generally refers to a length of sheet material spirally wound about a core. Rolled products include both a log of sheet material having a width dimension similar to the parent roll from which it is derived, and individual rolled products that have been divided into individual products intended for use by a consumer and which have a width substantially less than the parent roll from which it is derived. In certain instances, a rolled product may comprise a length of sheet material comprising one, two, three or more plies, having a plurality of perforations extending in the cross-machine direction of the sheet and spaced apart from one another in the machine direction to define individual sheets there between, the sheet material being spirally wound about a core.

As used herein the term "theoretical sheet caliper" ($C_T$) generally refers to the theoretical caliper of a sheet necessary to achieve substantially zero compressibility of a rolled product. Theoretical sheet caliper may be calculated based upon the diameter of the rolled product ($D_{sp}$), the diameter of the core used to form the rolled product ($D_C$), the machine direction distance between adjacent perforations ($L_{Perf}$) and the number of sheets in the product ($N_{sheet}$) as provided in Equation 2, below.

$$C_T = \frac{\pi \times [D_{sp}^2 - D_c^2]}{4 \times L_{perf} \times N_{sheet}} \quad \text{Equation 2}$$

The terms "web" and "sheet" are used herein interchangeably and generally refer to a planar sheet material, particularly fibrous sheet materials and more particularly fibrous sheets formed from cellulosic materials and having a basis weight from about 10 grams per square meter (gsm) to about 100 gsm. Webs and sheets may be converted into tissue products such as bath, facial and towel products, comprising one, two, three or more individual plies. In certain instances, webs and sheets may be converted into rolled tissue products by spirally winding one or more plies of sheet material around a core.

DETAILED DESCRIPTION

The present invention provides an adaptive control system to control a plant using direct output feedback in which a function of the full plant state, as opposed to estimates thereof, is used for feedback control of the plant. The adaptive control system of this invention is therefore highly useful in the control of plants, particularly plants for controlling the physical properties of rolled products produced from sheet material and more particularly a calendering apparatus. Accordingly, in a particularly preferred embodiment the adaptive control system of this invention controls loading of a calender apparatus, such as a pair of opposed rolls forming a calendering stack, based upon the physical properties of a previously processed web.

In particularly preferred instances the adaptive control system of the present invention may be applied to a process for converting a parent roll of web material into smaller, individual rolls by calendering a length of web to a desired caliper and winding the web about a core to produce a rolled product having a desired firmness. Because the incoming web properties vary depending upon where in the parent roll they originated from, the degree of calendering needed to achieve a desired finished product property, such as caliper and roll firmness, may vary. The present system may be used to vary the calendering as needed to overcome these variables and produce products having the desired properties.

While firmness, measured as the load spring constant, and/or sheet caliper, may be used as direct output feedback to control the load applied by the calender unit to the sheet, the relationship between the sensed physical properties and calender load may be non-linear in certain instances. That is, the effect of calender load on log spring constant and/or caliper may be more dramatic at lower calender loads than at higher loads. To account for this non-linearity gain scheduling may be employed. For example, the sheet caliper controller's gains may be modified to linearize the relationship between calender load and caliper by providing a function based on sample data and the current calender load generates the appropriate gain. Thus, in certain embodiments, the present invention provides a control system comprising a gain-scheduled controller augmented by an adaptive controller. For example, as will be in discussed in more detail below, the system may comprise an adaptive controller consisting of an adaptive component, a gain-scheduled calender load controller, a caliper sensor and an actuator.

Generally, the system of the present invention comprises one or more controllers that can receive measurement data from one or more sensors and use the data to control one or more operations within the plant. For example, a controller may use the sensor data to adjust any of the actuators or other components of the plant. The controller can include any suitable structure for controlling the plant or at least part of the plant, such as a computing device.

The controller and various components of the plant, such as actuators and sensors, may be coupled to one another by a network. The network can facilitate communication between components of the system. The network can represent any suitable network or combination of networks facilitating communication between components in the system. The network could, for example, represent a wired or wireless Ethernet network, an electrical signal network (such as a HART or FOUNDATION FIELDBUS network), a pneumatic control signal network, or any other or additional network(s).

In one embodiment, the system of the present invention includes an adaptive variable controller in communication with a gain-scheduling controller to control a calender unit. They may be configured to receive input from a parent roll diameter sensor and the gain-scheduling controller may receive input from a caliper sensor. In other embodiments the gain-scheduling controller may also receive input from a linear controller, particularly a log spring constant cascade controller, which is in communication with a firmness sensor.

In particularly preferred embodiments the adaptive variable controller may be configured, for instance, to calculate a calender load value for the calender unit and, based on this information, control the calender unit should the firmness or the caliper of the finished rolled product become outside of predetermined ranges. In this manner, through the system, the caliper of the web and/or the firmness of the finished rolled product may be controlled within predetermined ranges such that each of the finished rolled products produced by the plant has substantially uniform and desirable characteristics.

For example, in one embodiment, the pressure applied by a calender unit to a web unwound from a parent roll may be controlled such that the calendered web has a constant caliper. Over time the adaptive variable controller may receive direct output feedback from one or more plant sensors to vary the load applied by the calender to maintain a constant sheet caliper. In this manner the calender load may be varied dependent on the diameter of the parent roll from which the web is being unwound, as well as direct output feedback from one or more plant sensors.

In particularly preferred instances at least two product properties, such as firmness of the finished rolled product and the caliper of the web after calendering, may be sensed and used by the adaptive variable controller to control the calender unit for selectively increasing or decreasing the caliper of the web. In this manner at least two plant outputs may be used by the adaptive variable controller to optimize the operation of the plant.

Through the system of the present invention, rolled products can be produced having uniform and desired physical properties such as firmness and roll diameter. Various other advantages are also possible through the present invention.

For instance, the system of the present invention can also be used to control the caliper of the web of material that is presented to the winding device. By controlling the caliper of the web, the amount of tension placed on the web during winding and the firmness of the finished rolls is also controlled.

Generally, the first step in improving one or more properties of a finished rolled product is generating a relationship equation, also referred to herein as a reference model, for each of the averaged measured properties that correlates each of the $X^{th}$ measured properties. Initially this comparison will be done by inspecting outputs of the system over time and looking for immediate trends in the data before proceeding to the more statistical correlations. This initial comparison can be focused on looking for possible correlations between the physical property of the finished rolled product and the parent roll from which it is derived. After the initial inspection, an analysis tool can then be used to develop correlations between these desired variables. Alternatively, one skilled in the art could employ alternate technical methods that rely more on the modelling and simulation techniques to determine the variable correlations.

In a particularly preferred embodiment, a reference model correlating parent roll diameter and the calender load needed to achieve a desired web caliper may be developed. For example, to implement the control system a reference model may be established whereby the load applied to the rolls of a calender stack are varied depending upon the diameter of the parent roll being unwound and fed to the calender stack to achieve a desired sheet caliper. The reference model, which may also be referred to more particularly as a calender load curve, may consist of a plurality of individual data points, such as 5, 6, 7, 8, 9, 10 or more individual data points. In certain instances, the reference model may provide for a lower calender load to achieve the desired web caliper for webs originating from the outer diameter of the parent roll compared to those originating from the inner diameter.

One example of a reference model useful in the present invention is illustrated in FIG. 1. Generally, as the diameter of the parent roll is decreased, i.e., unwound and fed to the calender stack, the load applied to the calender stack is varied. As illustrated in FIG. 1, to achieve a desired finished product web caliper the load applied to the calender stack may initially be low and increased rapidly as the parent roll is unwound. The calender load then increases more gradually as the parent roll continues to be unwound before decreasing quickly as the parent roll diameter approaches zero.

Figure 2:
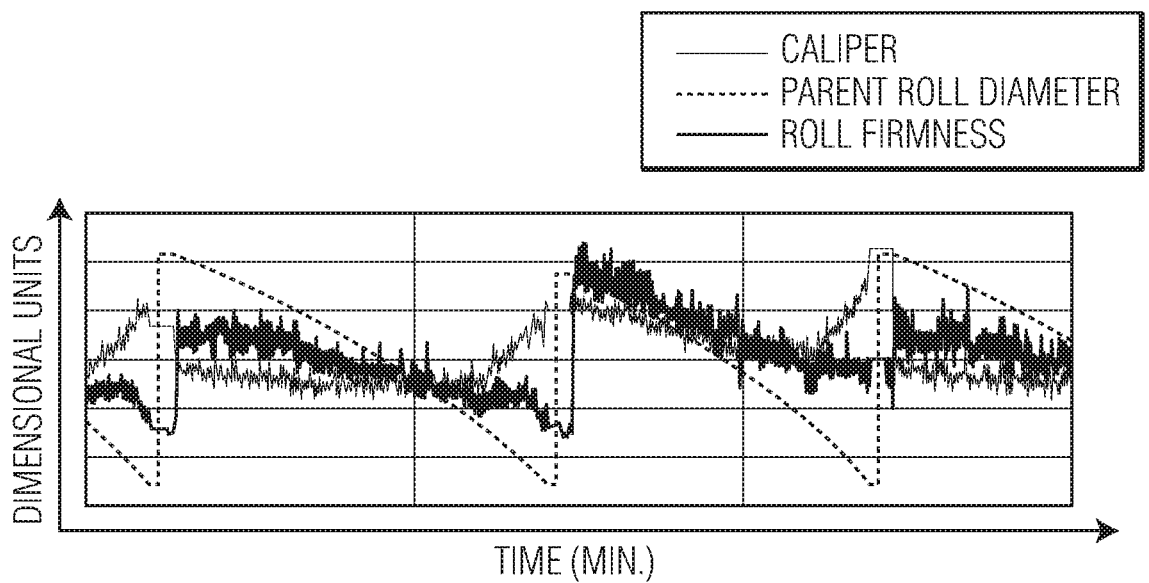
FIG. 2 is a graph of calender load and finished rolled product firmness over time for a control system without adaptive variable control to control the plant.
Figure 3:
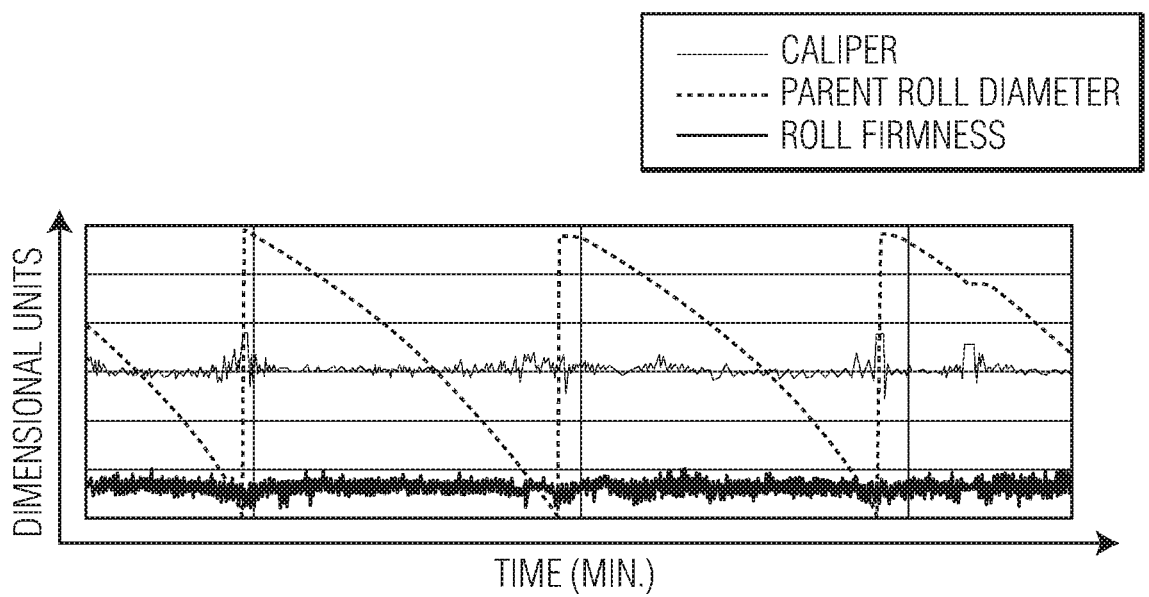
FIG. 3 is a graph of calender load and finished rolled product firmness over time for a control system with adaptive variable control to control the plant.

The adaptive control system of the present invention may be configured to sense certain web and roll properties, such as web caliper and roll firmness, and these properties may be used to optimize the established model. For example, the adaptive control system of the present invention is applied, the imperially established calender load curve may be optimized based upon feedback from the plant and be used to control future plant operations. In this manner the adaptive control system may improve plant operation and reduce finished product variability. For example, as shown in FIGS. 2 and 3, variability in the roll firmness and caliper of individual wound web products may be reduced throughout the entire diameter of a parent roll when the adaptive control system of the present invention is employed.

Figure 4:
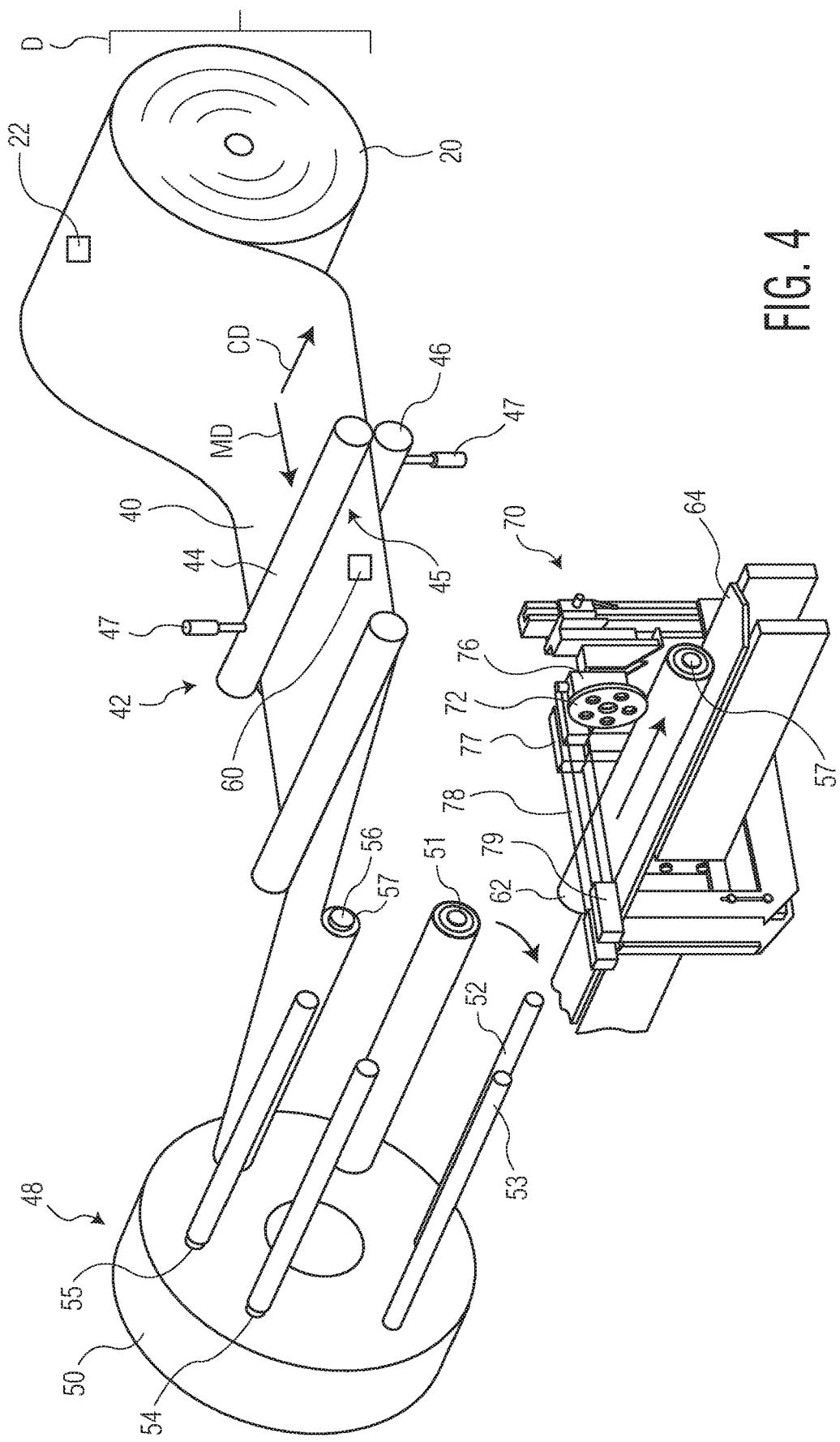
FIG. 4 illustrates a process for manufacturing a roll of web material according to one embodiment of the present invention.

With reference now to FIG. 4, one embodiment of a system for forming rolled products is illustrated. Although the system in FIG. 4 may form rolls of any type of material, the system is particularly well suited for forming paper rolls, such as rolls of bath tissue or paper towels. Such products are typically formed from sheets comprising cellulose fibers such as wood pulp fibers and have a bulk of at least 2 cc/g and more preferably at least about 5 cc/g. The sheets may comprise one, two, three or more plies and may have a basis weight from about 10 to about 100 gsm, such as from about 10 to about 60 gsm.

As shown in FIG. 4, in this embodiment, a web 40 having a machine direction (MD) and a cross-machine direction (CD) is unwound from a parent roll 20 having a diameter (D). Generally, an individual parent roll may be used to produce a plurality of individual rolled web products with the parent roll diameter being continually reduced with the winding of each individual product. The diameter (D) may be sensed using a diameter sensor 22, such as non-contacting and contacting sensing devices well known in the art. In certain instances, the diameter sensor may be a displacement sensor, which detects changes in parent roll diameter as it is unwound.

As the web 40 is unwound from the parent roll 20 it is fed through a calendering device 42 comprising a pair of spaced apart top and bottom rolls 44, 46. The rolls 44, 46 form a nip 45 through which the web 40 is fed. The rolls 44, 46 may be steel rollers, rubber-coated rollers, or mixtures thereof. In certain instances, one or more of the rolls may be provided with an engraved pattern, such as an embossing pattern, to impart a pattern to the web in addition to controlling the caliper.

The amount of pressure applied to the web 40 as it passes through the nip 45 may be controlled by moving one or more of the rolls 44, 46 relative to the other using one or more actuators 47. As the web 40 passes through the nip 45 pressure is applied by the opposed rolls 44, 46 and the caliper, also referred to as the thickness, is reduced. Generally, increasing the load applied by the calender to the web reduces caliper. In other instances, particularly where the unit of operation to be controlled is an embosser, increasing the pressure may affect the clarity or depth of embossments imparted to a web in addition to controlling the web caliper.

In certain instances, such as that illustrated in FIG. 4, the caliper of the web 40 after it passes through the nip 45 may be measured using a caliper sensor 60. Sheet caliper may be measured using a single sensor, such as illustrated in FIG. 4, or may be measured using multiple sensors. Suitable caliper sensors for use in the present invention include, for example, full contact, semi-contact, or contactless sensors known in the art. Particularly preferred are non-contact caliper sensors, which do not physically contact either side of the web material. In certain instances, the noncontact caliper sensors may project a spot onto each side of the web material and perform triangulation to measure web caliper as it is continuously conveyed through the plant. In other instances, the one or more noncontact caliper sensors project illumination lines onto the web material and measures the web material caliper at the intersection of those lines.

From the calendering device 42, the web 40 is fed to a log winding device 48. In general, any suitable log winding device may be used in accordance with the present invention. For instance, the winding device may be a surface winding device, a center winding device, a coreless winding device, and the like. In the embodiment illustrated in FIG. 4, the winding device 48 is a center winding device comprising six mandrels 51, 52, 53, 54, 55, 56 rotatably mounted to a turret 50. Although the winding device 48 is depicted as including six mandrels 51, 52, 53, 54, 55, 56, it should be understood that only one mandrel or any number of mandrels greater than one can be affixed to the turret 50. In other embodiments, it should be understood that a turret assembly is not needed. For instance, in an alternative embodiment, a surface winder may be used.

The winding process is generally initiated by placing a core (core 57 illustrated as loaded onto mandrel 56) onto the mandrel according to any method known in the art. The core may be loaded onto the mandrel at a "core loading position" of the turret 50, such as the position of mandrel 53 as shown in FIG. 4. Once the core is placed onto a mandrel 56, the turret can then be indexed into an "adhesive application position", which is the position occupied by mandrel 54 in FIG. 4. In this position, any suitable adhesive (not shown) can be applied to the core by any method known in the art.

After the adhesive is applied, the web contacts the adhesive and winding of the web onto the core begins, such as the winding of the web 40 onto the core 57 on mandrel 56. After the web is wound onto the core the mandrel may then be indexed by the turret into a "tail seal and removal position", which is the position occupied by mandrel 51 in the embodiment illustrated in FIG. 4. At the "tail seal and removal position", the end portion of the web can be sealed to the roll of material using any suitable sealing device. The sealing device may be configured, for instance, to apply glue or some other adhesive to the end of the web of material such that the tail can be sealed to the roll.

Figure 5:
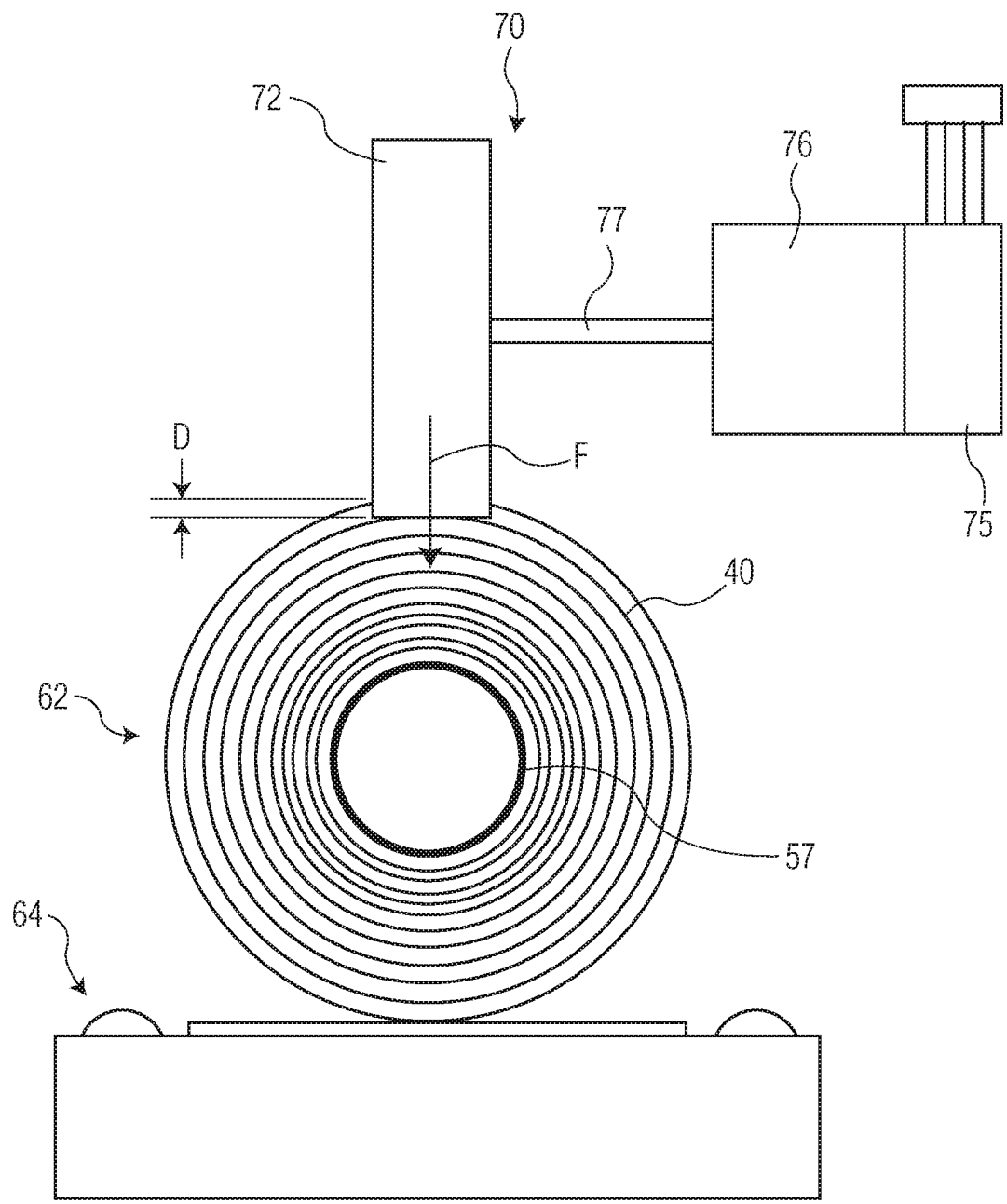
FIG. 5 is a detailed view of a firmness measurement device useful in the present invention.

Once the end of the wound web has been sealed, the finished log 62 may then be removed onto the conveyor 64, which transports the log 62 into contact with a firmness detection device 70. The firmness detection device 70 (shown in detail in FIG. 5) may comprise a contact element 72 that contacts the finished log 62. As shown, contact element 72 is a wheel or a roller. In other embodiments, however, a stationery shoe may be used that has a low friction surface.

As the finished log 62 passes under the contact element 72, the contact element 72 exerts a force (F) against the log 62 as a predetermined impingement depth (D) of the element 72 into the log 62 is maintained. The amount of force required to maintain the predetermined impingement depth (D) is measured by a force measuring device, such as a load cell 76. The load cell may be, for instance, in one embodiment a strain gauge. The load cell 76 is mounted to a pneumatic cylinder 75 for moving the load cell 76 vertically along with the contact element 72, which may be connected to the load cell 76 by a shaft 77.

The contact element 72 may be set up to impinge into the finished roll 62 a predetermined distance. The load cell 76 then records the force required to maintain the predetermined impingement distance as the finished log 62 is conveyed along the conveyor 64. Based upon the load cell reading, the log spring constant of the finished log, which is equal to force over displacement and may have units of Newtons per millimeter, may be calculated. A finished roll product that is difficult to compress, i.e., has a relatively high degree of firmness, will have a higher force reading at a given impingement distance and therefore a higher log spring constant.

In addition to the force placed against the contact element the firmness detection device 70 comprises a diameter measuring device 77. Suitable diameter measuring devices include, for example, devices such as those disclosed in U.S. Pat. No. 7,079,263, the contents of which are incorporated herein by reference. For example, as illustrated in FIG. 4, the diameter measuring device 70 may include, a pair of focused light sources or lasers 77 and a corresponding pair of light sensors 79 positioned opposite the lasers. When the finished log 62 is moved on the conveyor 64 adjacent to the diameter measuring device 77, the log 62 intersects the curtains of light 78 being emitted by the lasers 77. Light sensors measure the difference in light intensity caused by the intersection of the light curtains. This information can then be used to determine the diameter of the roll.

From the diameter of the finished roll, the distance between the contact element and the conveyor, and the amount of force measured by the load cell, a roll firmness value may be calculated as is known in the art. In certain embodiments the diameter of the finished roll may be assumed and the foregoing diameter measuring device may be omitted.

Figure 6:
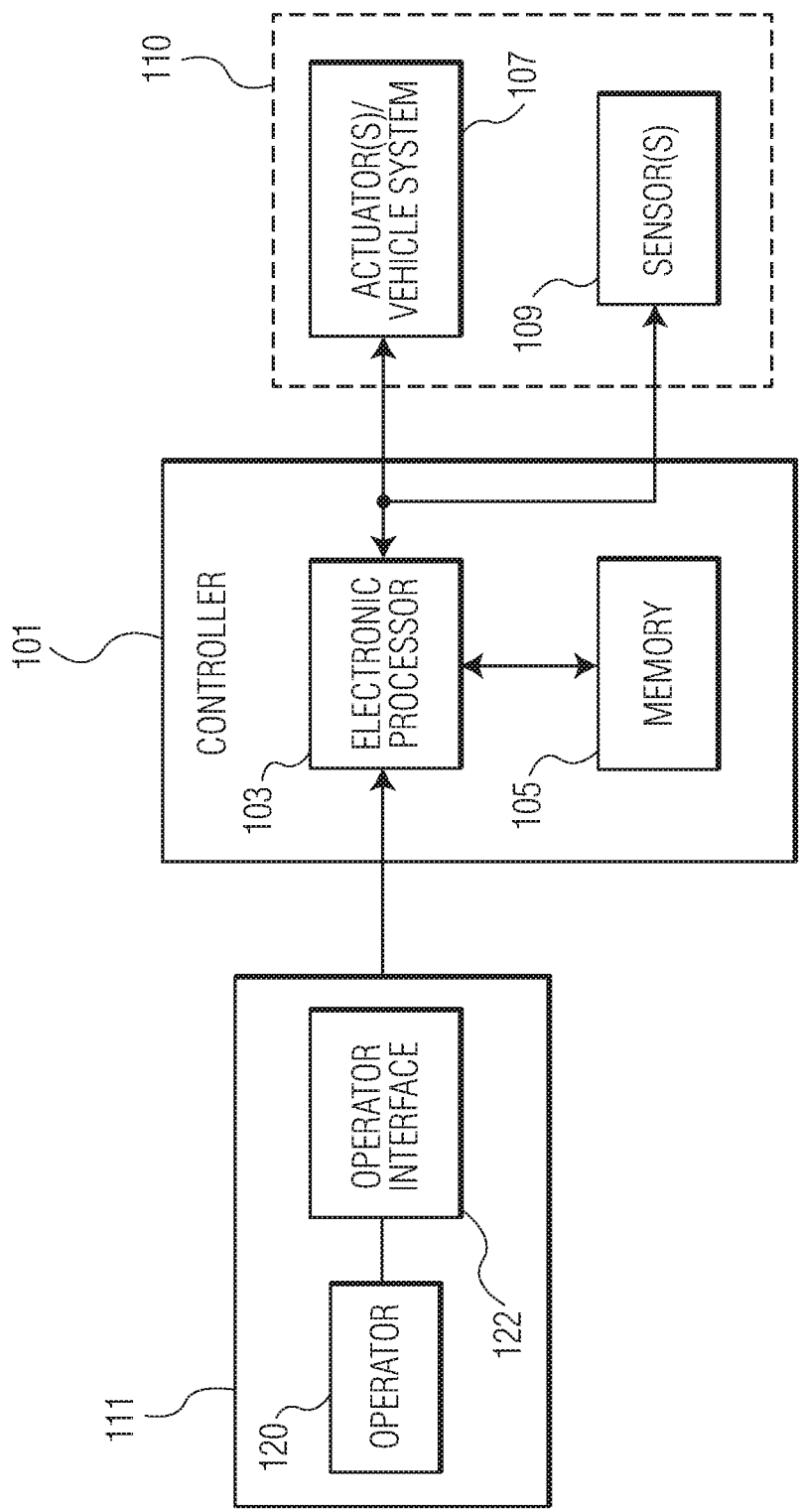
FIG. 6 is a block diagram of a control system for a rolled product converting operation according to one embodiment of the present invention.

With reference now to FIG. 6, which illustrates an example of a closed-loop, feedback-based control system for a plant 110, which in certain preferred embodiments may be a rolled product converting operation comprising a calendering apparatus and a winder, such as that illustrated in FIG. 4. The control system includes a controller 101, which includes an electronic processor 103 that is communicatively coupled to a computer-readable, non-transitory memory 105. The memory 105 stores instructions that, when executed by the electronic processor 103, causes the controller to provide various functionality of the system including certain functionality as described herein. The controller 101 is communicatively coupled to one or more actuators 107 and is configured to provide a control signal to the actuator(s) 107 to dictate the operation of the actuator(s) 107. The controller 101 is also communicatively coupled to one or more sensors 109 that monitor one or more performance variables of the system being controlled by the system of FIG. 6. The controller 101 is also configured to receive user control input from one or more user control(s) 111.

The user control 111 may comprise an operator 120 and an operator interface unit 122. These elements permit the operator 120, which can be human or machine, to interact with the adaptive controller 101 to control the plant 110, which generally comprises a system to be controlled. In certain instances, the system may be a non-linear system comprising one or more actuators for acting on and controlling the pressure of a pair of opposed rolls in a calender system. In addition to a calender system, the plant may comprise a winding device for producing a plurality of wound finished products.

Figure 7:
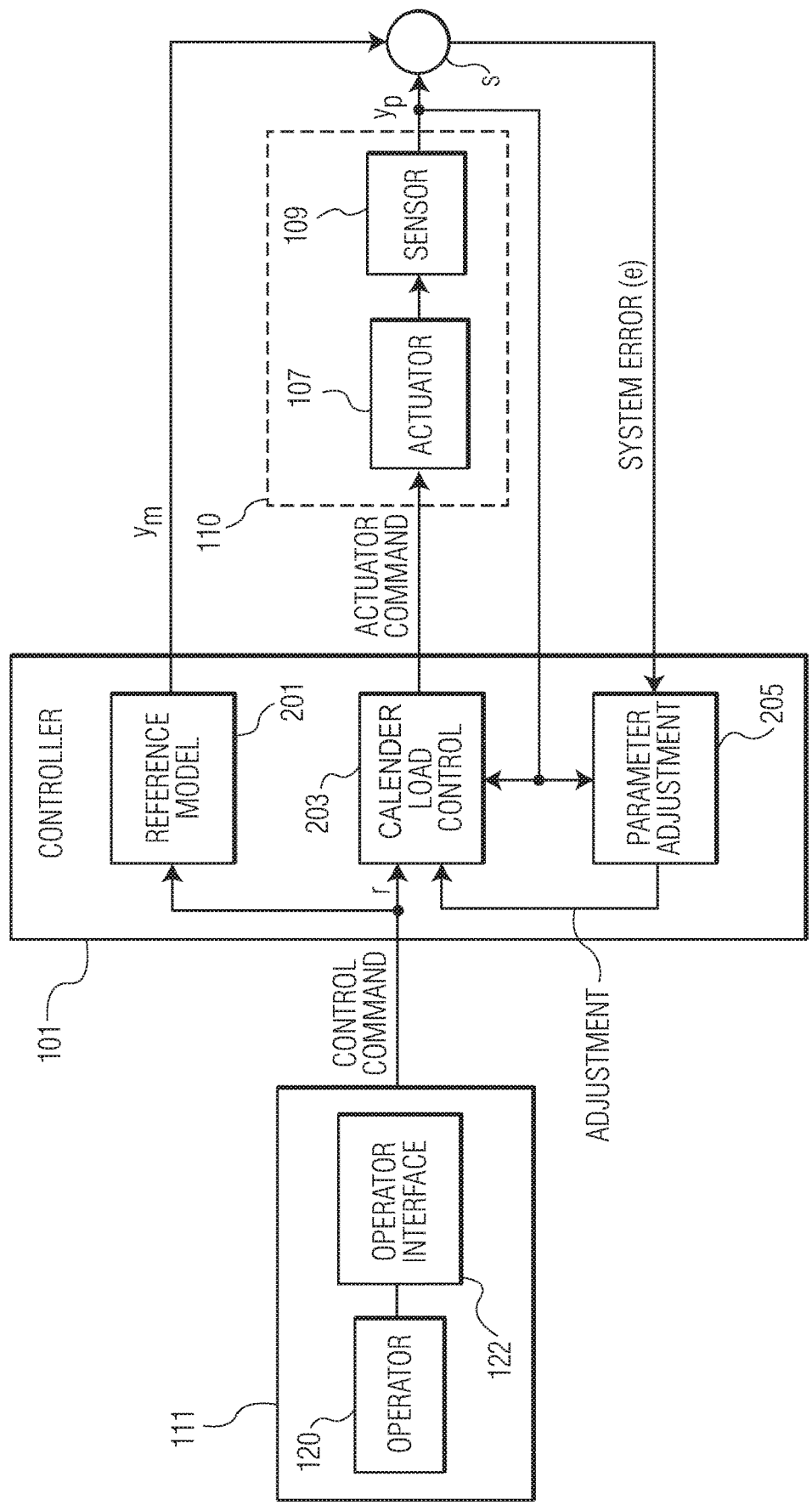
FIG. 7 is a block diagram of a model reference adaptive control (MRAC) for controlling a rolled product converting operation according to one embodiment of the present invention.

With reference now to FIG. 7, which illustrates an example of a method implemented by the controller 101 for controlling the operation of the plant 110 using a model reference adaptive controller (MRAC) mechanism. The controller 101 receives a control command from the user control 111 indicative of a desired task to be performed, such as adjusting one more calender trim inputs. The controller 101 applies the control command as an input to a reference model 201 to determine a target behavior or action to be performed in response to the control command from the user control 111. The controller 101 also applies the control command as an input to a calender load control 203 that determines an appropriate actuator command, which is then transmitted as a control signal from the controller 101 to the actuator 107. The controller 101 then monitors an output from a sensor 109 to determine how the system responded to the actuator command. The actual performance of the system, as indicated by the output of the sensor 109, is then compared to the expected performance as determined by the reference model 201. The difference between the actual performance and the expected performance is identified as a system error. The controller 101 is configured to apply a parameter adjustment 205 that subsequently adjusts the actuator command provided by the calender load control 203 to the actuator 107. In this way, the controller 101 is configured to use feedback to minimize the system error and, consequently, the actual performance approaches the expected performance. The control architecture illustrated in FIG. 7 enables the controller 101 to adapt to changes in the actuator/system itself due to degradation in such a way that the system continues to operate as expected (i.e., actual performance matches/approaches expected performance).

With continued reference to FIG. 7, the adaptive controller 101 comprises a reference model 201, a parameter adjustment mechanism 205 and a calender load control 203. The closed-loop dynamical system response (ye) is captured by the parameter adjustment mechanism 205 and compared to the reference model 201 by the comparator (S). The system error signal (e) resulting from this comparison drives the parameter adjustment mechanism 205, which then adjusts one or more controller parameters in a real-time (i.e., online) manner for driving the trajectories of the closed-loop dynamical system to the trajectories of the reference model 201.

The adaptive controller 101 controls the plant 110 based on the closed-loop plant output ($y_p$), the reference model output ($y_m$), a bounded reference signal (r) and the system error signal (e). The model reference adaptive controller 101 automatically adjusts calender load control 203, which in certain preferred embodiments may be a gain-scheduled calender load control, parameters so that the behavior of the closed-loop control plant output ($y_p$) closely follows that of the reference model output ($y_m$.) In this manner the reference model 201 is chosen to generate the desired trajectory ($y_m$) that the plant output ($y_p$) has to follow. The tracking error (e), which may generally be expressed by Equation 3 below, represents the deviation of the plant output ($y_p$) from the desired trajectory ($y_m$).

$$e \triangleq y_p - y_m \quad \text{Equation 3}$$

In certain embodiments, the object of the present invention is to choose a suitable model of calender loading at a given parent roll diameter to achieve a desired finished roll product firmness and caliper and provide a corresponding identification, or adaptation, algorithm which will identify the calender load with the comparison by the comparator leading to a match between the states of the reference model and the states of the adjustable model.

In practice the plant output ($y_p$), which in certain preferred instances is a calender load trim command, is received by the comparator (S) and compared to the reference model 201 to generate an error (e). The error (e) is received by the parameter adjustment mechanism 205 and used to vary the parameters of the control system, particularly a calender load trim command. Generally, the parameter adjustment mechanism 205 applies an adaptation law that attempts to find a set of parameters that minimize the error between the plant and the model outputs. The set of parameters generated by the adjustment mechanism 205 are communicated to the calender load control 203, which provides a calender load trim command to an actuator controlling the calender nip pressure.

In addition to a model reference adaptive controller 101, the present system may also comprise one or more feedback loops. For example, with reference to FIG. 8, the system may comprise a first outer feedback loop 312 and a second inner feedback loop 310. In certain instances, the first outer feedback loop 312 may be a roll firmness feedback loop, particularly a log spring constant (LSC) feedback loop, and the second inner feedback loop 310 may be a sheet caliper (SC) feedback loop.

Figure 8:
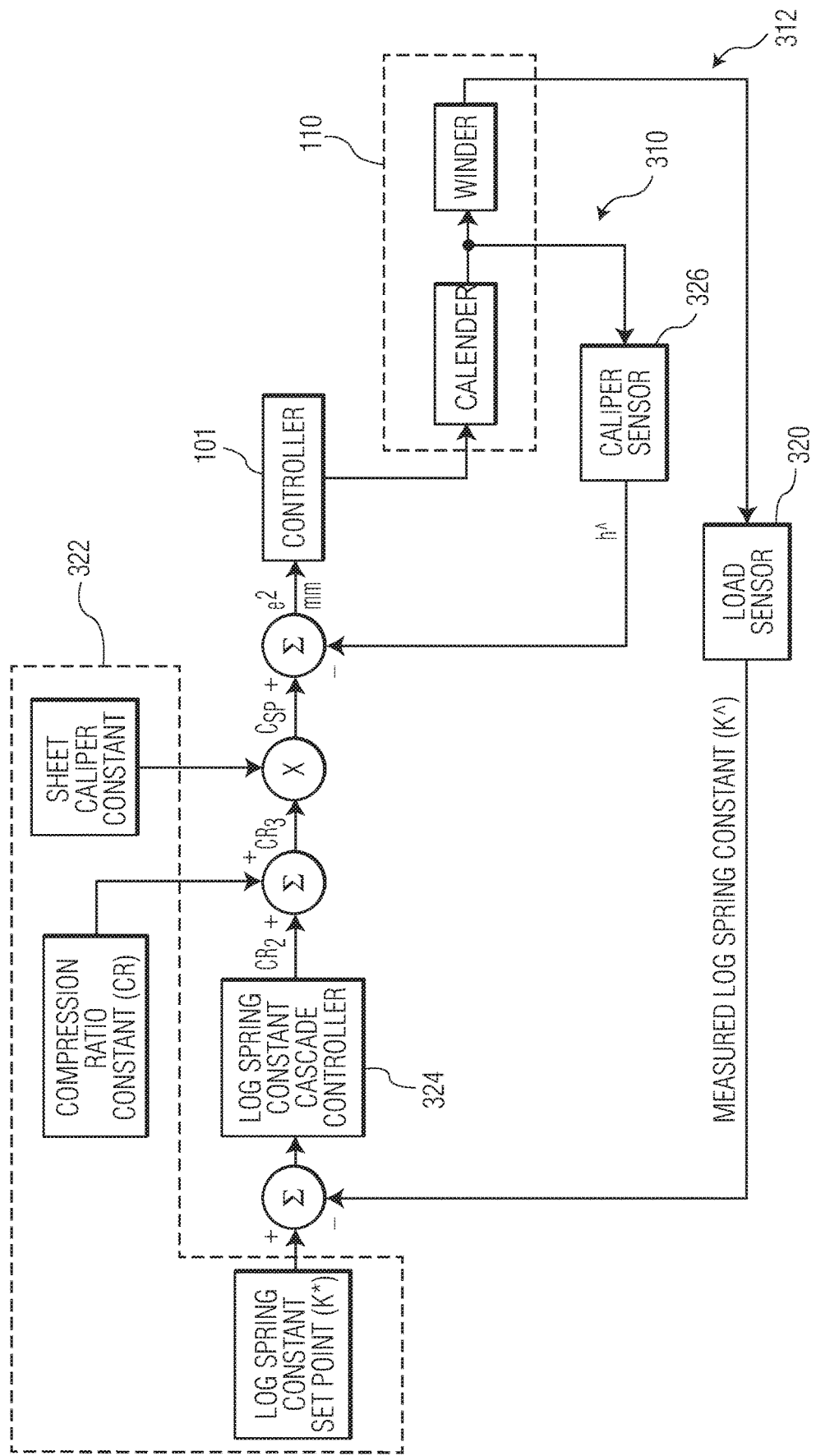
FIG. 8 is a block diagram of a control system for controlling a rolled product converting operation according to one embodiment of the present invention.

With continued reference to FIG. 8, the first outer feedback loop 312 comprises a load sensor 320, particularly a load sensor configured to measure the force required to impinge a contact element into a rolled product such as those discussed above. The load sensor 320 generates a sensed load value based upon the measurement of a rolled product, typically having units of force per unit distance, such as Newtons per millimeter. The measured value may be referred to the measured log spring constant (K^).

The measured log spring constant is compared with a log spring constant set point (K*) provided to the system by an operator 322. The difference between the measured log spring constant and the log spring constant set point is provided to a log spring constant cascade controller 324. The log spring constant cascade controller 324 provides a compression ratio adjustment command ($CR_2$), which is summed with the expected compression ratio, also referred to as a compression ratio constant (CR), provided by an operator and typically a constant derived based upon similar previously produced rolled products. The summed value is referred to herein as the combined compression ratio ($CR_3$).

Based upon the combined compression ratio (p3) and the theoretical sheet caliper ($C_T$) needed to achieve a desired roll firmness, which is calculated by an operator using Equation 2 above, and provided to the system, a sheet caliper set point ($C_{SP}$) may be calculated using Equation 4 and provided by the operator 322. The theoretical sheet caliper ($C_T$) is generally calculated based upon a finished product diameter ($D_{sp}$), the diameter of the core used to form the product ($D_C$), the length of the wound web between perforations applied thereto ($L_{Perft}$), the number of sheets in the product ($N_{sheet}$).

$$C_{SP} = C_T \times \left(1 + \frac{CR}{100}\right) \quad \text{Equation 4}$$

The sheet caliper set point ($C_{SP}$) may then be compared to the sheet caliper measured by the system (h^) and the result of the comparison ($e^2$) may be fed forward to the adaptive sheet caliper controller 101, which may adjust the load applied by the calender based upon the comparison.

With continued reference to FIG. 8, the second inner feedback loop 310 generally comprises a sheet calender feedback loop based upon the sensed sheet caliper after the web has been calendered. A caliper sensor 326, which may be a non-contact caliper sensor, senses the web caliper (h^) after calendering. The sensed web caliper (h^) is fed forward and compared to the sheet caliper set point ($C_{SP}$), which may be calculated as described above and generated as part of the first outer feedback loop 312.

While either firmness, measured as the log spring constant, or sheet caliper may be used as direct output feedback to control the load applied by the calender unit, the relationship between both values and calender load may be non-linear in certain instances. That is, the effect of calender load on either the log spring constant and/or the caliper may be more dramatic at lower calender loads than at higher loads. In certain instances, one or more of the controllers of the present system may be configured with gain scheduling as is known in the art to account for any non-linearity. For example, the sheet caliper controller's gains may be modified to linearize the relationship between calender load and caliper by providing a function based on sample data and current calender load generates the appropriate gain.

In addition to feedback from the plant, the adaptive controller 101 may be configured to receive the output of one or more processes upstream of the plant 110, such as from the parent roll unwind processes and more particularly from a parent roll diameter sensor. In this manner the adaptive controller 101 may be continuously provided with the diameter of a parent roll being unwound and processed by the plant 110.

In still other embodiments the control systems of the present invention may be used to control the tilt and crown of a caliper control apparatus, such as a pair of opposed rolls in a calender stack. In this manner the system may apply an adaptive control scheme to control cross-machine directional (CD) log spring constant of rolled products produced as disclosed herein. By controlling cross-machine directional (CD) log spring constant, the invention may be used to produce rolled products having a uniform feel and roll structure regardless of its position relative to the cross-machine direction of the caliper control apparatus.

Figure 9A:
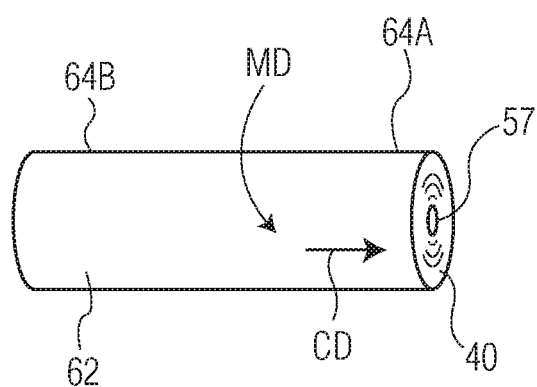
FIGS. 9A and 9B illustrate a roll of tissue product produced by an apparatus of the present invention and a plot of log spring constant for a plurality of cross-machine direction positions.
Figure 9B:
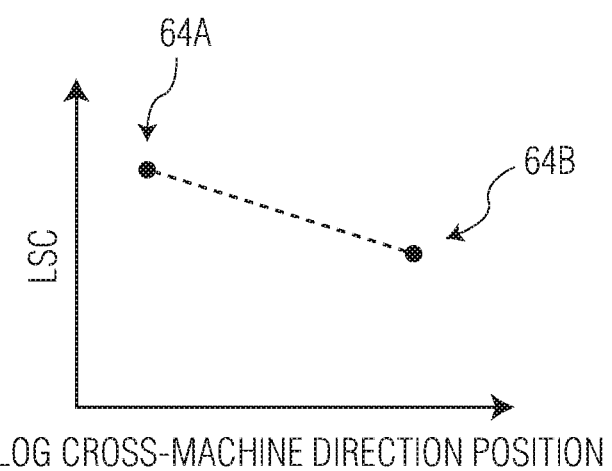

In one instance, to control the cross-machine direction log spring constant, a cross-machine direction profile of a finished product is constructed by measuring the log spring at a plurality of locations along the cross-machine direction of the finished product. For example, with reference to FIG. 9A, the finished product may comprise a web 40 spirally wound about a core 57 and having machine direction (MD) and cross-machined direction (CD). The log spring constant (LSC) may be measured, as described above, along at least two CD positions 64A, 64B of the roll 100. The measured log spring constants may then be plotted versus the relative CD position, such as illustrated in FIG. 9B. In certain instances, the log spring constant at a given CD position may be measured for several rolls and the values averaged to create a plot like that illustrated in FIG. 9B.

Generally, plots having a negative slope, such as shown in FIG. 9B, are indicative of a roll having higher firmness at a first end of the roll compared to the second end of the roll. This cross-machine variability is generally undesirable; thus, the present system may be used to adjust the calender load at a first and second end of the calender stack to produce rolls having a firmness, measured as log spring constant, that is substantially uniform across the CD of the roll. According, an adaptive control scheme according to the present invention may be used to adjust the load applied across the CD of the calender control unit to produce a roll having the desired CD log spring constant profile.

For example, with reference to FIG. lithe calender tilt controller 107 is an adaptive control and comprises a reference model, such as the model described below, a parameter adjustment mechanism and a calender load control. The tilt controller 107 is configured to receive the measured roll spring constant for a plurality of CD positions of a roll, generate a slope value, and compare the measured slope value to the reference model to generate an error (e). The error (e) is received by the parameter adjustment mechanism and used to vary the parameters of the control system, particularly a calender load tilt command. Generally, the parameter adjustment mechanism applies an adaptation law that attempts to find a set of parameters that minimize the error between the plant and the model outputs. The set of parameters generated by the adjustment mechanism are communicated to the calender tilt controller 107, which provides a calender load tilt command to an actuator controlling the calender nip pressure.

The tilt controller 107 may be configured as an adaptive controller to provide a suitable model for controlling the calender loading at a given calender cross-machine direction position to achieve a desired finished roll product firmness and provide a corresponding identification, or adaptation, algorithm which will identify the calender load with the comparison by the comparator leading to a match between the states of the reference model and the states of the adjustable model. In certain instances, an operator may provide the system with a reference model, such as Equation 5, and the adaptive controller will control the calender to achieve a slope ($\beta_1$) of zero.

$$\beta_1 = \frac{n \times \sum_{i=1}^{n}(x_i \times y_i) - \sum_{i=1}^{n} x_i \times \sum_{i=1}^{n} y_i}{n \times \sum_{i=1}^{n} x_i^2 - \left(\sum_{i=1}^{n} x_i\right)^2} \qquad \text{Equation 5}$$

In Equation 5, above, n is the number of CD positions measured for a given roll, x is the CD position of the measurement, and y is the measured log spring constant at a given CD position.

In other embodiments the control systems of the present invention may be used to control the crown of a caliper control apparatus, such as a pair of opposed rolls in a calender stack. Whereas the tilt controller may be used to adjust the calender load for a second end of a calender stack, control of the calender control may be used to control the pressure applied by the calender stack across the entire cross-machine direction of the stack. For example, the pressure applied to a web at the first and second ends of the calender stack may be different than the pressure applied to the web at the middle of the calender stack.

Figure 10A:
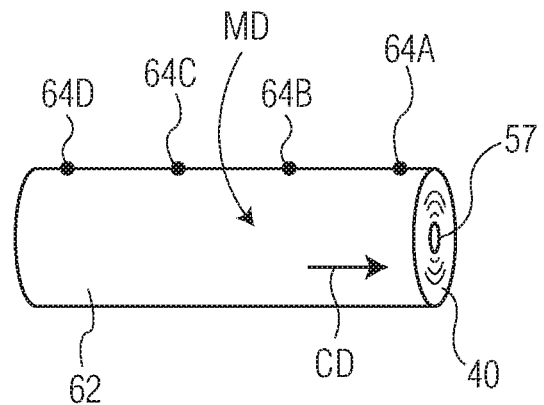
FIGS. 10A and 10B illustrate a roll of tissue product produced by an apparatus of the present invention and a plot of log spring constant for a plurality of cross-machine direction positions.

Generally, the first step in controlling the crown of a caliper control system is to generate a CD profile of a finished product by measuring the log spring at four or more cross-machine direction positions of a finished rolled product. For example, as illustrated in FIG. 10A, the log spring constant may be measured, as described above, at four CD positions 64A, 64B, 64C, 64D. The measured log spring constants may then be plotted versus the relative CD position, such as illustrated in FIG. 10B to generate a CD profile of a finished product.

Figure 10B:
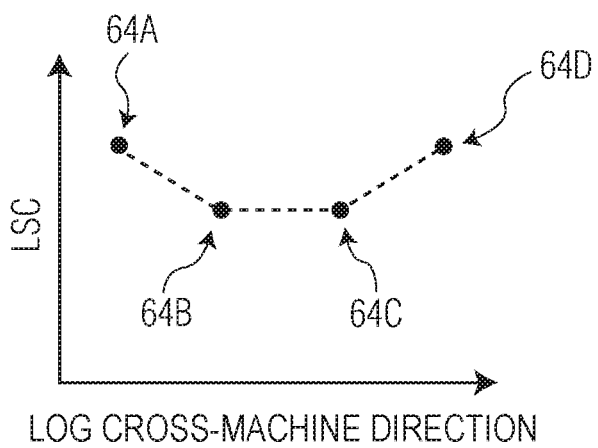

For finished rolled products having a concave shaped CD, such as shown in FIG. 10B, the roll has similar degrees of firmness at either end, but the middle portion is less firm. Again, it is generally desirable to produce rolls having substantially uniform firmness across the CD of the roll. Accordingly, an adaptive control scheme according to the present invention may be used to adjust the load applied across the cross-machine direction of the calender control unit to produce a roll having the desired CD log spring constant profile.

Figure 11:
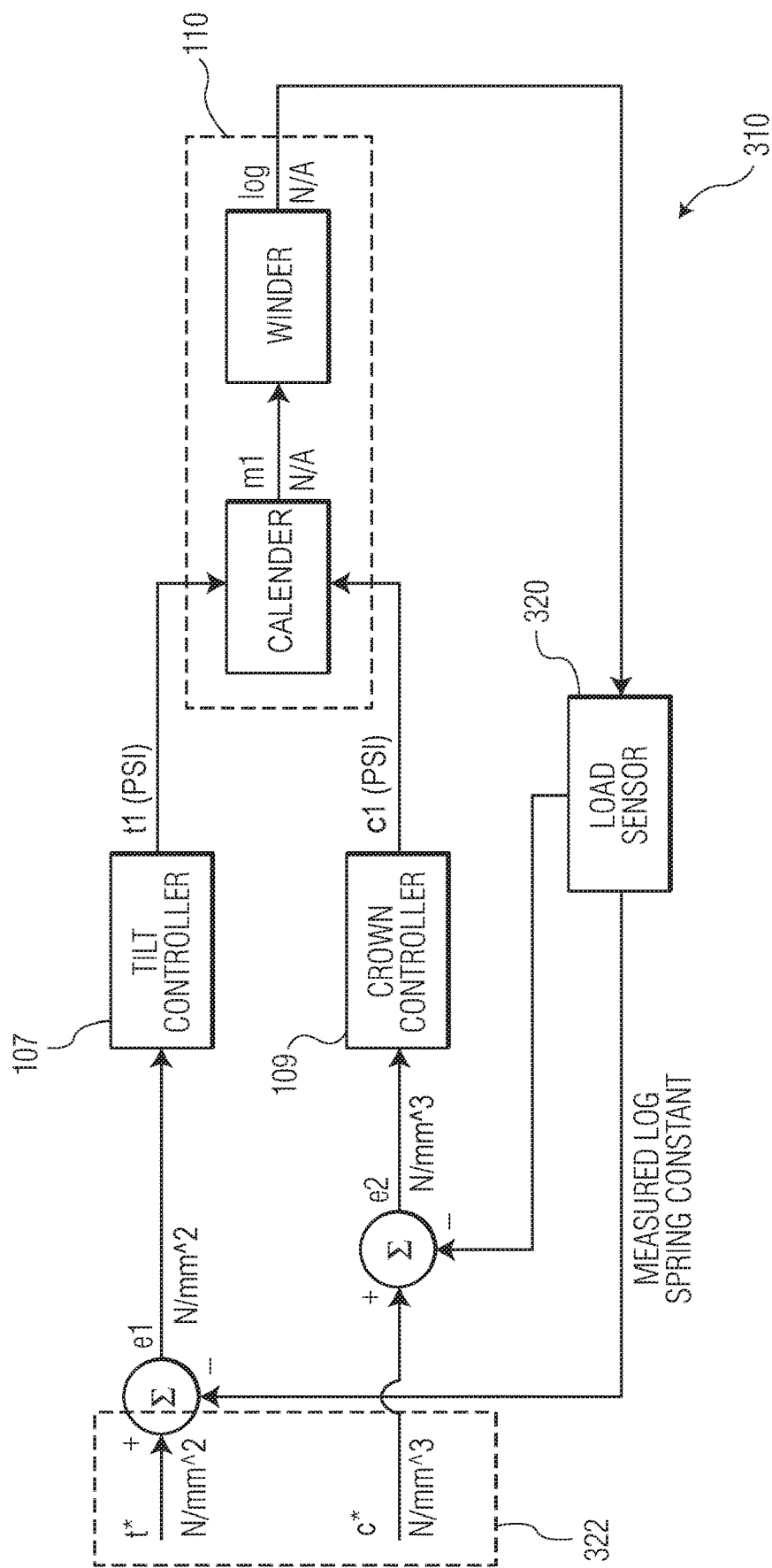
FIG. 11 is a block diagram of a control system for controlling a rolled product converting operation according to another embodiment of the present invention.

For example, with reference again to FIG. 11, an operator may provide a suitable model for controlling the calender loading at a given calender cross-machine direction position to achieve a desired finished roll product firmness and provide a corresponding identification, or adaptation, algorithm which will identify the calender load with the comparison by the comparator leading to a match between the states of the reference model and the state of the adjustable model. In certain instances, an operator may provide the system with a reference model, such as Equation 6, and the adaptive controller will control the calender such that $\beta_2$ equals zero.

$$\beta_2 = \frac{n \times \sum_{i=1}^{n}(y_i \times x_i^2) - \sum_{i=1}^{n} x_i^2 \times \sum_{i=1}^{n} y_i}{n \times \sum_{i=1}^{n} x_i^4 - \left(\sum_{i=1}^{n} x_i^2\right)^2} \quad \text{Equation 6}$$

In Equation 6, above, n is the number CD positions measured for a given roll, x is the CD position of the measurement, and y is the measured log spring constant at a given CD position.

What is claimed is:

1. A method for operating a system which regulates the load applied to a calender apparatus by one or more actuators during the converting of a parent roll of spirally wound sheet material and having a parent roll diameter into individual finished rolled products of spirally wound sheet material comprising the steps:
    (a) generating a reference model;
    (b) providing a first operating state of the system to regulate the load applied to the calender apparatus by the one or more actuators depending upon the diameter of the parent roll and the reference model;
    (c) sensing at least one characteristic of the finished rolled product with a sensor and generating at least one sensor output;
    (d) communicating the at least one sensor output;
    (e) receiving the at least one sensor output by a comparator;
    (f) using the at least one sensor output in an adaptive control scheme whereby the at least one sensor output received by the comparator is compared to the reference model to generate a system error and the system error is used by a parameter adjustment mechanism to determine the load to be applied to the calender apparatus by the one or more actuators in a second operating state of the system; and
    (g) adjusting the load applied to the calender apparatus by the one or more actuators according to the second operating state.

2. The method of claim 1 wherein the sensor outputs are sheet caliper and log spring constant.

3. The method of claim 1 wherein the sensor outputs are sheet caliper and log spring constant and further comprising the step of calculating the difference between a log spring constant set point and the sensed log spring constant.

4. The method of claim 3 further comprising the step of providing the calculated difference to a log spring constant cascade controller and generating a compression ratio adjustment command.

5. The method of claim 4 furthering comprising the step of summing the compression ratio adjustment command with a compression ratio constant.

6. The method of claim 1 further comprising the steps of calculating a sheet caliper set point ($C_{SP}$) and comparing Csp to the sensed sheet caliper and using the comparison in the adaptive control scheme.

7. A system for regulating the load applied to a calender apparatus by one or more actuators during the unwinding of a parent roll of sheet material and having a parent roll diameter into individual finished products of spirally wound sheet material, the system comprising: (a) one or more sensor interfaces for receiving sensor outputs from one or more sensors that sense a characteristic of the individual finished rolled products; and (b) a processing circuit configured to provide a first operating state and an adapted operating state;
    wherein the load applied to the calender apparatus by one or more actuators is varied dependent upon the diameter of the parent roll being unwound;
    wherein the processing circuit is configured to receive the sensor inputs from the one or more sensor interfaces and to determine and adjust the first operating state using an adaptive control scheme whereby the sensor inputs received by processing circuit is compared to a reference model to generate a system error and the system error is used by a parameter adjustment mechanism to determine the load to be applied to the calender apparatus by the one or more actuators in a an at least one adapted operating state; and
    wherein the processing circuit is further configured to cause the system to transition from the first operating state to the least one adapted operating state.

8. The system of claim 7 wherein the one or more sensors comprise a sheet caliper sensor and a load sensor.

9. The system of claim 7 wherein the sensed characteristics are sheet caliper and log spring constant.

10. The system of claim 7 wherein the one or more sensors comprise a load sensor and further comprising a log spring constant cascade controller for receiving the output from the load sensor and generating a compression ratio adjustment command.

11. The system of claim 10 wherein the load sensor comprises a contact element positioned a fixed distance from a support surface and force sensing device for measuring a force applied to a finished rolled product placed between the contact element and the support surface.

12. The system of claim 7 wherein the one or more sensors comprise a sheet caliper system and the processing circuit receives a comparison of the sheet caliper set point ($C_{SP}$) and the sheet caliper measured by the sheet caliper sensor.

13. The system of claim 12 wherein the sheet caliper sensor comprises a non-contact sheet caliper sensor.

14. The system of claim 7 wherein the plurality of sensors comprises a sheet caliper sensor, a load sensor and a finished rolled product diameter sensor.

15. A system for regulating the load applied to a calender apparatus during the converting of a parent roll into individual finished rolled products, the system comprising:
    (a) an adaptive controller comprising a reference model, a parameter adjustment mechanism and a calender load control;
    (b) an actuator for controlling the position of at least one calender roll in a calender stack;
    (c) a caliper sensor for sensing the caliper of a calendered web;
    (d) a load sensor for sensing a force applied to a contact element by a finished rolled product when the finished rolled product is placed in between the contact element and a support surface; and
    (e) a log spring constant cascade controller;
    wherein the adaptive controller is in communication with the actuator and the controller is configured to control the actuator for increasing or decreasing the caliper of a web of material based upon inputs from the caliper sensor and the load sensor.

16. The system of claim 15 wherein the log spring constant cascade controller receives the output from the load sensor and generates a compression ratio adjustment command.

17. The system of claim 15 wherein the adaptive controller receives a comparison of the sheet caliper set point ($C_{SP}$) and the sheet caliper measured by the sheet caliper sensor.

18. The system of claim 15 wherein the sheet caliper sensor comprises a non-contact sheet caliper sensor and the load sensor comprises a contact element positioned a fixed distance from a support surface and force sensing device.

19. The system of claim 15 wherein the load sensor is configured to sense a load at a plurality of cross-machine direction (CD) positions for a given finished rolled product to generate a CD profile of a finished product and the reference model consists of a model to minimize the slope or curvature of the CD profile.

* * * * *